Figure 1:
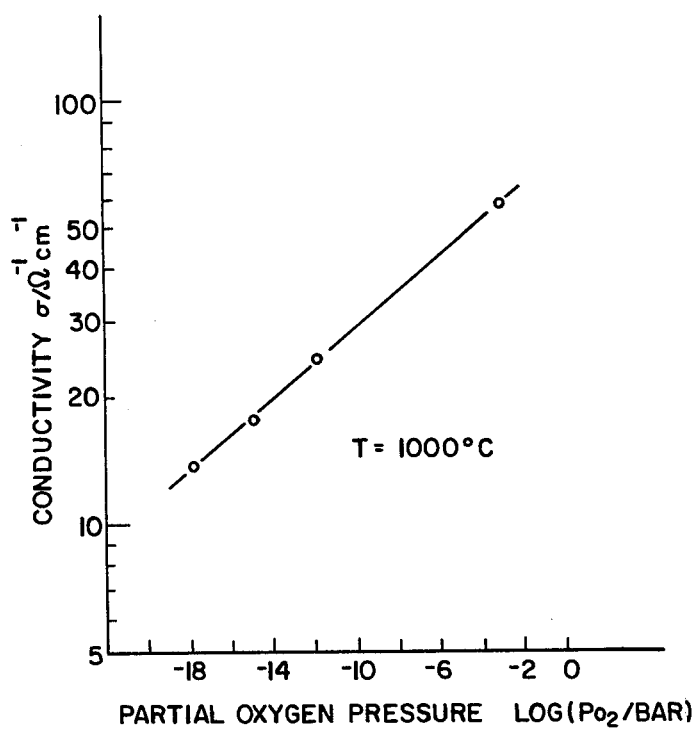

United States Patent [19]

Schmidberger et al.

[11] 4,276,202

[45] Jun. 30, 1981

[54] PROCESS FOR THE MANUFACTURE OF ELECTRODES HAVING PEROVSKITE STRUCTURE FOR ELECTROCHEMICAL HIGH TEMPERATURE CELLS

[75] Inventors: Rainer Schmidberger, Bermatingen; Wolfgang Dönitz, Immenstaad, both of Fed. Rep. of Germany

[73] Assignee: Dornier System GmbH, Fed. Rep. of Germany

[21] Appl. No.: 66,227

[22] Filed: Aug. 13, 1979

[30] Foreign Application Priority Data

Aug. 25, 1978 [DE] Fed. Rep. of Germany ....... 2837118

[51] Int. Cl.³ .................. B01J 21/10; B01J 23/06; B01J 23/10; B01J 23/26
[52] U.S. Cl. .................. 252/462; 204/290 R; 204/290 F; 204/291
[58] Field of Search ................. 252/462; 204/290 R, 204/290 F, 291; 423/595

[56] References Cited

U.S. PATENT DOCUMENTS

| | | | |
|---|---|---|---|
| 3,400,054 | 9/1968 | Ruka et al. | 204/195 S |
| 3,503,809 | 3/1970 | Spacil | 204/195 S |
| 3,929,670 | 12/1975 | Kudo et al. | 252/462 X |
| 3,974,108 | 8/1976 | Staut et al. | 423/595 X |
| 4,049,583 | 9/1977 | Lauder | 252/462 |
| 4,076,611 | 2/1978 | Gray | 204/290 F |

*Primary Examiner*—W. J. Shine
*Attorney, Agent, or Firm*—James E. Bryan

[57] ABSTRACT

This invention relates to a material for the manufacture of porous electrodes for electrochemical high temperature cells and measuring sondes having oxygen ion-conducting solid electrolytes based on zirconium dioxide or cerium dioxide, comprising an admixture of mixed oxides having a perovskite structure based on $LaMnO_3$ or $LaNiO_3$ or $LaCoO_3$, and small amounts of chromium and monovalent or bivalent cations selected from the group of the alkali elements or the alkaline earth elements or of Zn, Cd, Mg, Sn, or Pb. The invention also relates to a process for the manufacture of electrode material.

7 Claims, 2 Drawing Figures

PROCESS FOR THE MANUFACTURE OF ELECTRODES HAVING PEROVSKITE STRUCTURE FOR ELECTROCHEMICAL HIGH TEMPERATURE CELLS

The present invention relates to a material for manufacturing porous electrodes for electrochemical high-temperature cells and measuring sondes with oxygen ion-conducting solid electrolytes based on zirconium dioxide or cerium dioxide.

Electrochemical high-temperature cells with oxygen ion-conducting solid electrolytes work generally at an elevated operating temperature (500°–1000° C.). Employed as electrodes for such high-temperature cells are frequently porous solid electrodes which render possible a gas passage to the boundary surface of electrode-electrolyte. Examples of such electrodes are known from the literature. The requirements which are to be met by these electrodes depend very strongly upon the operating parameters of the electrochemical high-temperature cell, in which particularly the operating temperature and the composition of the gaseous atmosphere are the dominant parameters.

In some cases of application, the atmospheric composition to which the respective electrodes are exposed is relatively narrowly limited by the operating conditions of the cells. This holds true, for example, for high-temperature fuel cells, or high-temperature electrolytic cells, where, at an operating temperature of 1000° C., the partial oxygen pressure on the atmospheric electrode side varies between maximally $10^{-2}$ and 10–50 bars and, on the fuel gas side or water vapor side, it is within the range of between $10^{-12}$ and $10^{-18}$ bar.

In other cases of application, such as, for example, measuring sondes or electrochemical oxygen pumps, the partial oxygen pressure may vary over very wide ranges (for instance between 1 and $10^{-18}$ bar at 1000° C.).

For the cases of application mentioned first hereinabove with narrowly limited partial oxygen pressure ranges, electrode materials are known from the literature and from patents which materials largely meet the requirements placed on them.

Precious metal electrodes are practically no longer employed for these cases of application because materials with more favorable prices can perform the electrode functions. On the fuel gas- or water vapor side, non-precious metal electrodes, for example from nickel, cobalt, iron, copper, and the like may be used, whereby partially the installation of the porous electrodes into a ceramic supporting skeleton is effected. Such a nickel-zironium dioxide-cermet electrode has been described for example in U.S. Pat. No. 3,503,809.

At an operating temperature of 1000° C., the use of such a nickel electrode is limited to partial oxygen pressures below $10^{-10}$ bar.

For operation in an oxidizing gaseous atmosphere, electrode materials are equally known from the literature which consist of either metallic oxides or mixed oxides and which have an electronic conductivity that is below the metallic conductivity by about 2–3 decimal powers. A very high conductivity is displayed, in this connection, by mixed oxides with a perovskite structure which have been disclosed, for example, in U.S. Pat. No. 3,400,054. In a reducing atmosphere, the conductivity of these materials decreases very markedly and under certain circumstances there even occurs a disintegration of the perovskite structures.

In case the operating parameters of electrochemical high-temperature cells are varied only within narrow limits, the mixed oxide electrodes on the oxidizing side and non-precious metal electrodes on the reducing gas side, corresponding to the state of the art, thus represent a technically and economically advantageous solution.

For cases of application in which the electrodes are subjected to greatly varying partial oxygen pressures, the art knows only of precious metal electrodes (particularly porous platinum electrodes).

For example, by Dueker, Friese and Haecker in SAE (Techn. Paper) 1975, 750,223, platinum is employed as the exhaust gas electrode of a measuring sonde for exhaust gas control in motor vehicles.

German Offenlegungsschrift (DE-OS) No. 2,632,138, proposes precious metals such as Pt, Au or Ag for the air—and exhaust gas electrode of an oxygen measuring sonde.

These precious metal electrodes may be employed in the oxidizing as well as in the reducing atmosphere up to very high temperatures. They also partially display a frequently desirable catalytic activity for the adjustment of the thermodynamic equilibrium in the gas chamber (CO oxidation or $NO_x$-reduction).

Because of the high costs of precious metals, however, precious metal electrodes, and particularly platinum electrodes, are to be avoided, if at all possible, for economic reasons.

Apart from this economic disadvantage of platinum electrodes, there are also technical disadvantages, such as, for example, the formation of volatile platinum oxides at high temperature which, during long-term operation, may lead to complete degradation; as well as the tendency of platinum to form agglomerates because of its high surface tension at elevated temperatures, whereby the electrochemical efficacy of such electrodes is impaired.

It is the object of the present invention to provide an electrode made from favorably-priced starting materials which is thermodynamically stable over a wide partial oxygen pressure range and which has a sufficiently high electronic conductivity.

This object is attained, in accordance with the present invention, by virtue of the fact that added to mixed oxides with a perovskite structure based on $LaMnO_3$ or $LaNiO_3$ or $LaCoO_3$ are small amounts of chromium and monovalent or bivalent cations $La_{1-x} C_x Mn_{1-y} Cr_y O_3$ $La_{1-x} C_x Ni_{1-y} Cr_y O_3$ $La_{1-x} C_x Co_{1-y} Cr_y O_3$ $x = 0 \ldots 0.5$ $y = 0 \ldots 0.5$ C = alkali elements, alkaline earth elements, Zn, Cd, Mg. Sn or Pb.

In the present invention, individual elements in the electronically highly conductive mixed oxides are substituted by other elements, whereby the thermodynamic stability of the mixed oxide in the reducing atmosphere at high temperature is increased without a significant decrease of the electronic conductivity taking place at the same time. In addition thereto, the thermal expansion coefficient of the electrode material is adapted to that of the zirconium dioxide electrolyte ceramic material by suitable doping.

Figure 2:
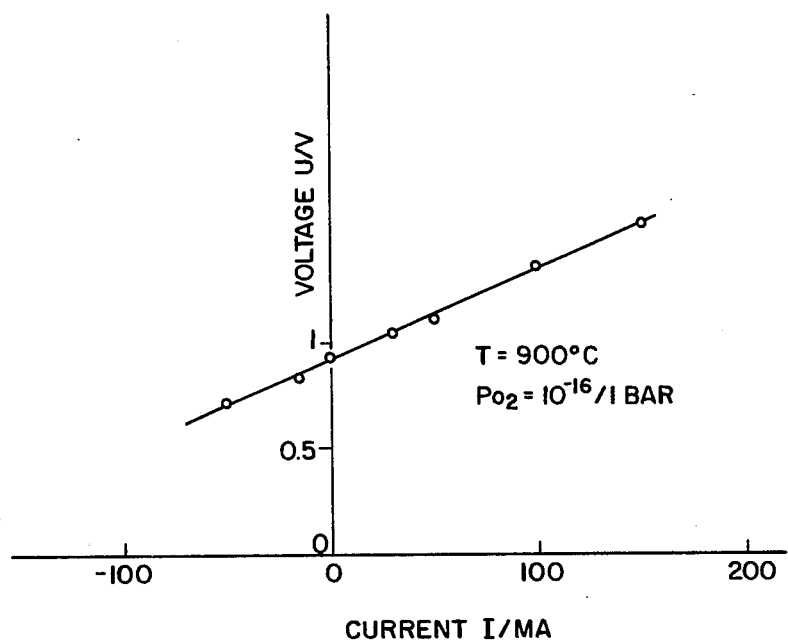

Further advantages, features, and possibilities of application of the present invention will become apparent from the accompanying drawings which will be described in further detail hereinbelow and wherein:

FIG. 1 is a diagram of the electronic conductivity of an inventive material in dependence upon the partial oxygen pressure, and FIG. 2 is a diagram of the current-voltage characteristic of a high-temperature cell.

An inventive material has the composition $La_{0.8}$, $Pb_{0.2}$, $Cr_{0.3}$, $Mn_{0.7}$, $O_3$.

FIG. 1 illustrates the electronic conductivity on the inventive material at 1000° C. in dependence upon the partial oxygen pressure. The conductivity changes by the factor 5 with a difference in the partial oxygen pressure of $10^{-18}$ bar.

FIG. 2 illustrates the current voltage characteristic of an electrochemical high-temperature cell with a solid electrolyte of stabilized zirconium dioxide, an inventive electrode, and a counter-electrode from a mixed oxide being stable only in the oxidizing atmosphere. The replacement of a part of the manganese ions by chromium ions in the inventive material results in an increase of the thermodynamic stability of the mixed oxide in the reducing atmosphere; i.e. the evolution of oxygen of the mixed oxide takes place at lower partial oxygen pressures than is the case without the chromium addition. The partial replacement of lanthanum by lead ions results in the adjustment of the thermal expansion coefficient to that of the stabilized zirconium dioxide.

The inventive material does not display the phase change, known in pure lanthanum-chromium oxide of orthorhombic-rhombohedral at 250° C. which is connected with a change of the lattice constants and would give rise to detachments of the electrode, or crack formations therein.

The catalytic activity of the material renders possible the adjustment of the thermodynamic equilibrium in the exhaust gas of combustion devices at the three-phase-boundary of the measuring probe, whereby—due to the lead constituent—the sensitivity of the electrode material with respect to poisoning by lead additives in the fuel is reduced.

In order to achieve, simultaneously, a high electronic conductivity and a high reduction stability of the mixed oxide, the chromium addition must be kept as low as possible and at the same time be made effective within the atomic range by as homogeneous as possible an element distribution.

This is accomplished, according to the present invention, by the production of the mixed oxide in a spray reaction process during which the oxides or other soluble compounds of the participating elements are initially dissolved in a stoichiometric ratio, and then atomized in a spray reactor under the influence of high temperatures, and yielded as a powder, while the solvent is separated, for example by means of a cyclone.

The spraying is effected at a temperature of about 1000° to 1500° K., in the presence of sufficient oxygen for reaction. Also, adjuvant substances may be added to the solution which is atomized and sprayed into the reactor, in order to improve the electrode adhesion or for increasing the porosity of the electrode. The adjuvant substance may be added to the solution in the form of a suspension or in the form of soluble compounds. Further, platinum or alloys thereof may be added to the solution which is atomized and sprayed, for the purpose of improving the catalytic activity of the material, thereby rendering possible an adjustment of the thermodynamic equilibrium in exhaust gases. The platinum or alloys thereof may be added to the solution in the form of a suspension or in the form of a soluble compound.

Not only are the desired material properties obtained in this manner, but at the same time the process eliminates a plurality of process steps that are otherwise customary for a powder production, such as the repeated mixing, pressing, calcining, and grinding of the oxide powder, and therefore may be realized also in an economically desirable manner. This is shown in the table below on the basis of a comparison of the process features.

The following materials, for example, are employed as adjuvant substances:

$Li_2O$: organic substances such as polyvinyl alcohol for increasing the porosity, $SiO_2$, $Bi_2O_3$: for improving the electrode adhesion.

TABLE

| | MANUFACTURE OF MIXED OXIDES | |
|---|---|---|
| starting products | conventional process<br>oxides, carbonates | spray-reaction drying<br>oxides, carbonates, nitrates, chlorides |
| manufacturing process | mixing of the individual powders<br>pressing of the powders<br>calcining of the pressed articles<br>(type 1200–1400°/24–28 h)<br>grinding<br>pressing<br>calcining | production of a joint solution<br>spraying-in (spray-calcining) |
| disadvantages | inhomogeneous distribution in<br>multi-component systems<br>volatility of specific oxides<br>sinter activity obtainable only by<br>long grinding<br>cost-intensive in multi-component<br>oxides due to 2 or 3 calcining<br>processes<br>adulterations or contaminations due<br>to grinding dust (or abrasion) | partially more expensive starting<br>products because of the insolubility<br>of some oxides ($Al_2O_3$, $ZrO_2$...) |
| advantages | easily available, inexpensive raw<br>materials | compositions being homogeneous up<br>into the atomic range, and resulting<br>therefrom excellent material properties<br>high sinter activity<br>high degree of purity of the end<br>products |

It will be obvious to those skilled in the art that many modifications may be made within the scope of the present invention without departing from the spirit thereof, and the invention includes all such modifications.

What is claimed is:

1. A process for the manufacture of electrode material having a perovskite structure for electrochemical high temperature cells and measuring sondes having oxygen ion-conducting solid electrolytes based on zirconium dioxide or cerium dioxide, comprising an admixture of mixed oxides based on $LaMnO_3$ or $LaNiO_3$ or $LaCoO_3$, and small amounts of chromium and monovalent or bivalent cations selected from the group of the alkali elements or the alkaline earth elements or of Zn, Cd, Mg, Sn, or Pb, which comprises spraying into a hot reaction zone a solution of metal compounds in a stoichiometric ratio and at a temperature of about 1000° to 1500° K., in the presence of sufficient oxygen for reaction, evaporating the solvent from the non-volatile constituents, whereby during further passage of the constituents through the hot reaction zone, mixed oxides are formed having the desired composition with homogeneous element distribution, particularly chromium distribution, in the atomic range, and separating said oxides from solvent vapors.

2. A process according to claim 1 including adding adjuvant substances to said solution for improving the electrode adhesion or for increasing the porosity of the electrode.

3. A process according to claim 2 including adding the adjuvant substances to the solution in the form of a suspension.

4. A process according to claim 2 including adding the adjuvant substances to the solution in the form of soluble compounds.

5. A process according to claim 1 including adding platinum or alloys thereof to said solution for improving the catalytic activity of the material, thereby rendering possible an adjustment of the thermodynamic equilibrium in exhaust gases.

6. A process according to claim 5 including adding platinum or alloys thereof to said solution in the form of a suspension.

7. A process according to claim 5 including adding platinum to said solution in the form of a soluble compound.

* * * * *

UNITED STATES PATENT AND TRADEMARK OFFICE
CERTIFICATE OF CORRECTION

PATENT NO. : 4,276,202
DATED : June 30, 1981
INVENTOR(S) : Rainer Schmidberger and Wolfgang Dönitz It is certified that error appears in the above—identified patent and that said Letters Patent is hereby corrected as shown below:

Column 5, line 1 of Claim 1, after "of" insert - - - porous - - -; line 5 of Claim 1, "comprising" is to be deleted and - - - consisting essentially of - - - , substituted therefor; line 11 of Claim 1, "metal compound" is to be deleted and - - - compounds of said metals - - - substituted therefor.

Signed and Sealed this

Fourteenth Day of September 1982

[SEAL]

Attest:

GERALD J. MOSSINGHOFF

Attesting Officer       Commissioner of Patents and Trademarks